US006241777B1

United States Patent
Kellan

(10) Patent No.: US 6,241,777 B1
(45) Date of Patent: Jun. 5, 2001

(54) PHAKIC INTRAOCULAR LENSES

(76) Inventor: Robert E. Kellan, 49 Sutton Hill Rd. No., Andover, MA (US) 01845

( * ) Notice: Subject to any disclaimer, the term of this patent is extended or adjusted under 35 U.S.C. 154(b) by 0 days.

(21) Appl. No.: 09/652,505

(22) Filed: Aug. 31, 2000

Related U.S. Application Data

(60) Provisional application No. 60/154,508, filed on Sep. 1, 1999, provisional application No. 60/152,690, filed on Sep. 7, 1999, and provisional application No. 60/151,991, filed on Sep. 17, 1999.

(51) Int. Cl.⁷ ..................................................... A61F 2/16
(52) U.S. Cl. ......................... 623/651; 623/6.54; 623/6.43
(58) Field of Search .................. 623/6.11, 6.38, 623/6.4, 6.42, 6.43, 6.51, 6.52, 6.54

(56) References Cited

U.S. PATENT DOCUMENTS

| | | | |
|---|---|---|---|
| 4,053,953 | 10/1977 | Flom et al. ................................. | 3/13 |
| 4,254,509 | 3/1981 | Tennant ...................................... | 3/13 |
| 4,285,072 | 8/1981 | Morcher et al. ........................... | 3/13 |
| 4,676,792 | 6/1987 | Praeger ..................................... | 623/6 |
| 4,710,195 | 12/1987 | Giovinazzo ............................... | 623/6 |
| 4,711,638 | 12/1987 | Lindstrom ................................. | 623/6 |
| 4,816,032 | 3/1989 | Hetland ..................................... | 623/6 |
| 4,994,080 | 2/1991 | Shepard .................................... | 623/5 |
| 5,133,747 | 7/1992 | Feaster ...................................... | 623/6 |
| 5,928,282 | 7/1999 | Nigam ....................................... | 623/6 |
| 6,015,435 | 1/2000 | Valunin et al. ............................ | 623/6 |
| 6,083,261 | 7/2000 | Callahan et al. .......................... | 623/6.38 |

Primary Examiner—Dinh X. Nguyen
(74) Attorney, Agent, or Firm—McDermott, Will & Emery

(57) ABSTRACT

An intraocular lens assembly for use in the phakic or aphakic eye is provided. In the preferred embodiment, the intraocular lens assembly is suitable for the correction of myopia, hyperopia, astigmatism.

The lens assembly has a lens having a circumferential edge, and a first haptic and a second haptic, which extend from the edge of the lens. Each of the haptics has a first leg extending from the lens edge to a distal end, and a second leg extending from the lens edge to distal end, and a transverse member extending between the distal ends of each first and second leg. The transverse member can be substantially straight or bowed inward toward the lens. Each leg has a footplate at its distal end.

Each leg of each haptic may be in inwardly bowing, straight, and outwardly bowing. Additionally, each leg may have the same or different shape from the other legs. In a one embodiment, the first and second legs of the first and second haptics are outwardly bowing. In another embodiment, the first and second legs of the first and second haptics are inwardly bowing.

The intraocular lens assembly is made from a flexible material. Preferably the material is hydrogel, collagen, collamar, collagel, acrylate polymers, polymethylmethacrylate polymers, silicone polymers, and composites thereof.

In another embodiment, the intraocular lens assembly is foldable. In another embodiment, the intraocular lens assembly is firm.

22 Claims, 6 Drawing Sheets

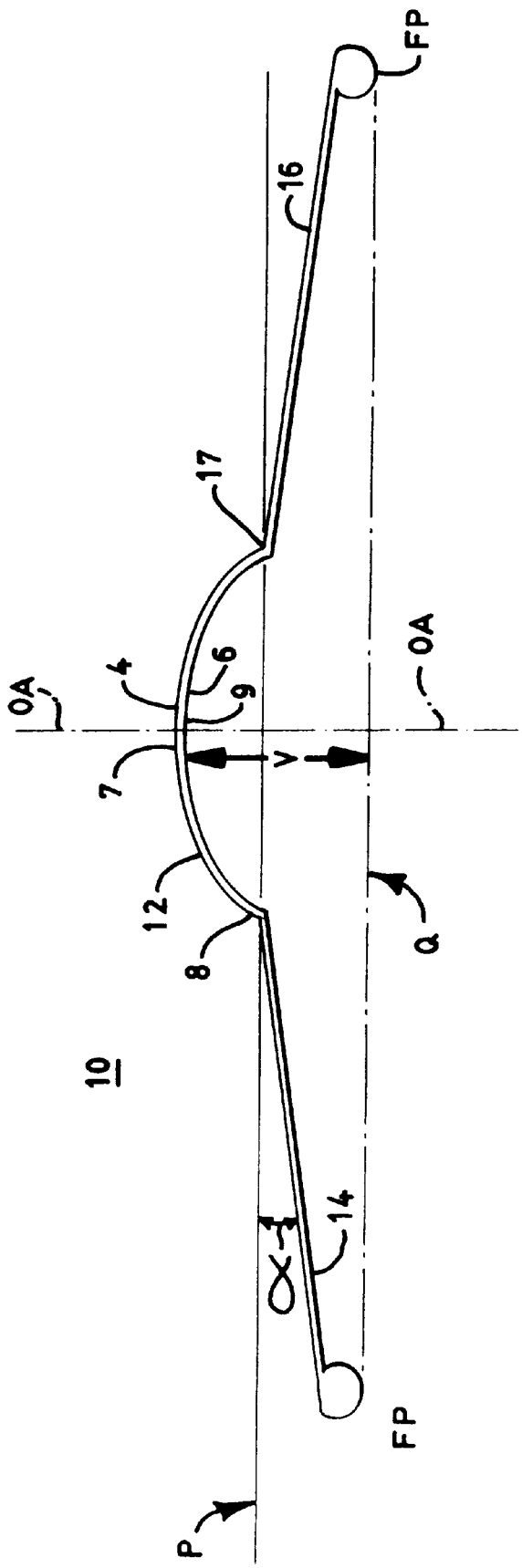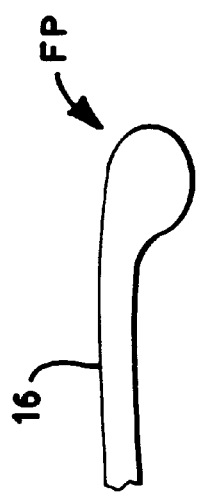
FIG. 2
FIG. 3

PHAKIC INTRAOCULAR LENSES

This application claims benefit to provisional application 60/151,991 Sep. 1, 1999 and claims benefit of 60/152,690 Sep. 7, 1999 and claims benefit of 60/154,508 Sep. 17, 1999.

FIELD OF THE INVENTION

The present invention relates to implantable intraocular lenses suitable for the correction of myopia, hyperopia, and astigmatism.

BACKGROUND

Implantation of lenses into the human eye has been a standard technique for many years, both to replace the natural crystalline lens (aphakic eye) and to supplement and correct refractive errors of the natural lens (phakic eye).

Various diseases and pathological conditions can result in damage to the natural crystalline lens, such as opacification that occurs as a result of cataracts. Intraocular lens implantation into the anterior chamber or posterior chamber of the eye is a known technique for treating cataracts.

Intraocular corrective lenses have been developed for the treatment of various vision problems of the eye, such as myopia, hyperopia and astigmatism in the phakic eye. However, the use of currently available phakic intraocular lenses has been less than satisfactory in the long term correction of refractive errors because the overall design of these lenses can result in damage to the natural crystalline lens.

The ideal phakic intraocular lens must be implantable through a self-sealing, clear corneal incision. It must be made of a very biocompatible material. It must have minimal touch with the uveal structures of the eye, no contact with the natural crystalline lens, and no compromise of the angle of the eye.

Currently, most phakic lenses are either iris-fixated lenses, angle fixated lenses or sulcusfixated, posterior chamber lenses.

Iris fixated lenses require a 5.5 to 6 mm incision and involve a difficult insertion surgical technique. Angle fixated lenses generally a 5.5 mm incision. These lenses also require very accurate white to white measurements, which are difficult to obtain. Angle fixated lenses can also cause pupillary distortion. Sulcus fixated/posterior chamber lenses are less difficult surgically to insert than iris fixated lenses but are more difficult to inset than angle fixated lenses. There have been reports of cataract formation after insertion of these lenses. Examples of implantable intraocular lenses include various design configurations. Generally, the lenses are attached in some manner within the eye, usually by sutures to the iris, or some other supporting means, such as arms, or haptics, extending from the optical lens portion of the intraocular lens.

U.S. Pat. No. 4,053,953 describes an artificial intraocular lens for the aphakic eye. The lens is secured in the posterior chamber by a system of posts that protrude through the iris attached to retaining rings.

U.S. Pat. No. 6,015,435 describes a self centering phakic intraocular lens inserted in to the posterior chamber lens for the correction of myopia, hyperopia, astigmatism, and presbyopia. Haptic bodies are attached to optical body and extend outward from tangent points at the edge of lens in at least two generally opposite directions. Protruding surfaces protrude into pupil such that the iris interferes slightly with lens movement and provides the centering force to keep lens in place.

U.S. Pat. No. 4,710,195 describes a posterior chamber lens, particularly adapted for patients with glaucoma and cataracts. Two haptics are connected to optic body at its edge. The haptics are offset from the other by 180 degrees and extend circumferentially around the edge of the optic portion. The haptics end in enlarged "blocking segments".

U.S. Pat. No. 4,676,792 describes an artificial intraocular lens device implantable in the anterior chamber of the eye (in front of the iris) for treating myopia. The optic body has three or four "J" shaped haptics which terminate with solid footplates to anchor the lens. In one embodiment, haptics are positioned circumferentially around the edge of optic body approximately 90 degrees apart. The haptics are grouped in pairs so that each pair is oriented such that the respective curved surfaces of solid foot plates face each other.

U.S. Pat. No. 5,133,747 describes an intraocular lens device that is partially or completely within the anterior capsular surface of the human crystalline lens. In one embodiment, the optic body has asymmetrical haptics extending outwardly from opposite sides of the periphery of the optic body. In one embodiment, "J" shaped haptics extend from the periphery of the optic body in a manner that encircles optic body. In another configuration, the haptics extend tangentially away from body, then reverse direction, giving the device an overall "S" shape with the lens at center portion of S. The device is secured in place with an adhesive.

U.S. Pat. No. 5,928,282 describes a refractive intraocular lens for implantation into the anterior chamber. The lens body has elongated, ovoid-disc shaped haptics extending from its peripheral edge.

U.S. Pat. No. 4,994,080 describes optical lens devices having an optical body with multiple perforations and two J shaped haptics which terminate in footplates.

U.S. Pat. No. 6,083,261 describes an intraocular lens having crossed haptics for implantation into either phakic or aphakic eye.

U.S. Pat. No. 4,285,072 describes closed loop haptics on an intraocular lens. When positioned in the eye, the circular arched haptics without footplates extend rearward from the optic body, then angle sideways to allow the arch to rest in the angle to keep the lens in place. This design proved to be physiologically unsuitable for use.

There is a need for an intraocular lens device that overcomes the problems of the existing intraocular lenses and yet provide ophthalmic surgeons with an intraocular lens that addresses the refractive errors in patients' eyes safely and reversibly. It is an object of the present invention to provide an intraocular lens that is made of existing biocompatible, FDA approved, flexible foldable materials. It is a further object of this invention to provide an intraocular lens that, because it is foldable, can be inserted through a small, self-sealing, clear corneal incision. It is yet a further object of the invention to provide an intraocular lens that is explantable through an incision the size of the original insertion incision. It is another object of the invention to provide an intraocular lens that has minimal contact with the anatomic structures of the eye.

SUMMARY

An intraocular lens assembly and method for correcting myopia, hyperopia and astigmatism using the intraocular lens assembly are provided. The lens assembly has a lens having a circumferential edge, and a first haptic and a second haptic, which extend from the edge of the lens. Each of the haptics has a first leg extending from the lens edge to a distal end, and a second leg extending from the lens edge to distal end, and a transverse member extending between the distal ends of each first and second leg. The transverse member can be substantially straight or bowed inward toward the lens. Each leg has a footplate at its distal end.

Each leg of each haptic may be in inwardly bowing, straight, and outwardly bowing. Additionally, each leg may have the same or different shape from the other legs.

In a one embodiment, the first and second legs of the first and second haptics are outwardly bowing. In another embodiment, the first and second legs of the first and second haptics are inwardly bowing.

The intraocular lens assembly is made from a flexible material. Preferably the material is hydrogel, collagen, collamar, collagel, acrylate polymers, methacrylate polymers, silicone polymers, and composites thereof.

In another embodiment, the intraocular lens assembly is foldable. In another embodiment, the intraocular lens assembly is firm.

DESCRIPTION OF THE DRAWINGS

The invention, and the various features thereof, may be more fully understood from the following description, when read together with the accompanying drawings, in which:

FIG. 2 shows a cross sectional view of the lens assembly of FIG. 1 along axis A.

FIG. 3 shows a sectional view of one of the footplates of the lens assembly of FIG. 1;

DESCRIPTION OF THE INVENTION

The design of intraocular lens assembly of the present invention overcomes the problems with the prior intraocular devices. The intraocular lens of the present invention is primarily designed for placement in the anterior chamber of the eye and use as a refractive lens for the phakic eye. However, the unique design of the intraocular lens also permits its use in the aphakic eye, and placement in the posterior chamber sulcus and the posterior chamber bag. The intraocular lens assembly described herein is suitable for correction of myopia, hyperopia, and astigmatism without compromising the anatomy or physiology of the eye.

The intraocular assembly of the present invention is made from a biocompatible, flexible, material. In a preferred embodiment, the material is also a foldable material, which allows insertion of the device through small incisions, usually 3 mm or less. Since the device is preferably inserted into the anterior chamber of the eye, there is no contact with the natural crystalline lens, cataract formation is minimized. The design provides minimal contact with other tissues in the eye. Furthermore, the device can be easily removed and reinserted as needed. The combination of flexible materials and the haptic design allows the device to withstand some deforming forces, such as the patient rubbing his eyes, without the device breaking, warping, or becoming disengaged from the eye.

Figure 1:
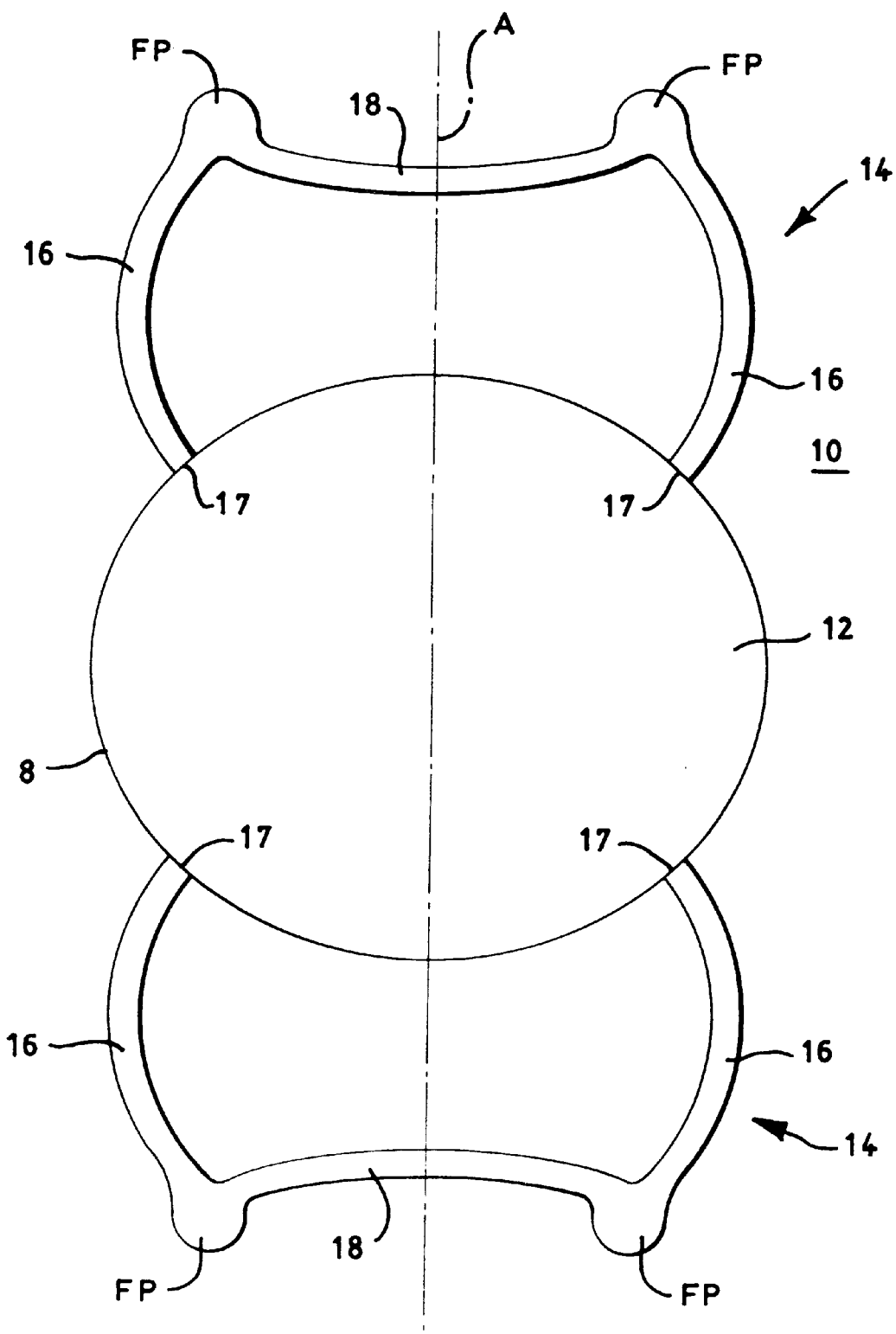
FIG. 1 shows a top view of the lens assembly of the invention.

As shown in FIG. 1, the intraocular lens assembly 10 includes a lens portion (the "optic") 12 and two sets of haptics 14 extending from periphery 8 of optic 12. Each set of haptics 14 has pair of legs 16 that connect at their proximal ends to periphery 8 at points 17, and extend toward footplates FP at their distal ends. Legs 16 are connected together in pairs substantially near their distal ends by transverse member 18. In the embodiment shown in FIG. 1, legs 16 are outwardly bowing, and each pair is joined by an inwardly bowing transverse member 18. Preferably, proximal ends of legs 16 are spaced equidistant around periphery 8 of optic 12. This symmetry provides the most comfort to the patient and stability of the lens. Alternatively, legs 16 may be attached at differently spaced, non-equidistant points on periphery 8 as needed, depending upon the individual eye anatomy or vision requirements.

FIG. 2 shows a cross section of the embodiment of FIG. 1 along axis A. Optic 12 constitutes the optical portion of the lens assembly. The optic 12 comprises a outer surface 4 and inner surface 6. The combination of inner surface 4 and outer surface 6 may result in the optical portion being substantially planar, convex, plano-convex and concave, bi-convex, concave-convex, or any combination thereof. Preferably, the shape is substantially concave-convex. The diameter of optic 12 can vary as needed to accommodate the angle to angle measurement of the eye and curvature of the eye. The overall length of the intraocular lens (optic and haptics) to be inserted into an individual patient's eye is determined by adding a 1 mm white-to-white measurement of the patient's eye. Optic 12 preferably has a 6 mm optical zone.

Optic 12 may be ground to the required diopter measurements necessary for vision correction. The lens may be a negative or positive meniscus lens and may include correction for astigmatism. Depending on the refractive index of the material used, and the required vision correction, optic 12 may have the same thickness at central portion 7 and periphery 8, or central portion 7 may be thinner than periphery 8. Preferably the thickness of optic 12 is 1 mm.

As shown in FIG. 2, haptics 14 extend from periphery 8 of optic 12 at a slight angle from a horizontal (as shown) axis P perpendicular optical axis OA. Depending upon the curvature and size of the optic lens needed, haptics 14 may be offset from horizontal axis P by angle α. Vault distance V is the height of the lens assembly measured from a line Q, which is drawn horizontally (as shown) between footplates FP, to the apex 9 of inner surface 6 and parallel to optical axis OA. Angle α may be 2 or 3° or more as needed, provided that angle α is one that, when in combination with the size and shape of the optical element and the anatomical angle of the eye, provides a 1 mm vaulting distance V. The vaulting distance insures adequate clearance for the intraocular lens assembly to be situated between the natural crystalline lens and the cornea in the anterior chamber.

The footplates FP of the haptics are integrally formed on the distal end of each leg 16, preferably near or at the point where leg 16 connects to the transverse member 18. Footplates FP are preferably lenticular-shaped (shown in FIG. 3) to allow for minimal contact with the eye structures yet provide the required stability for the desired visual results.

Figure 4:
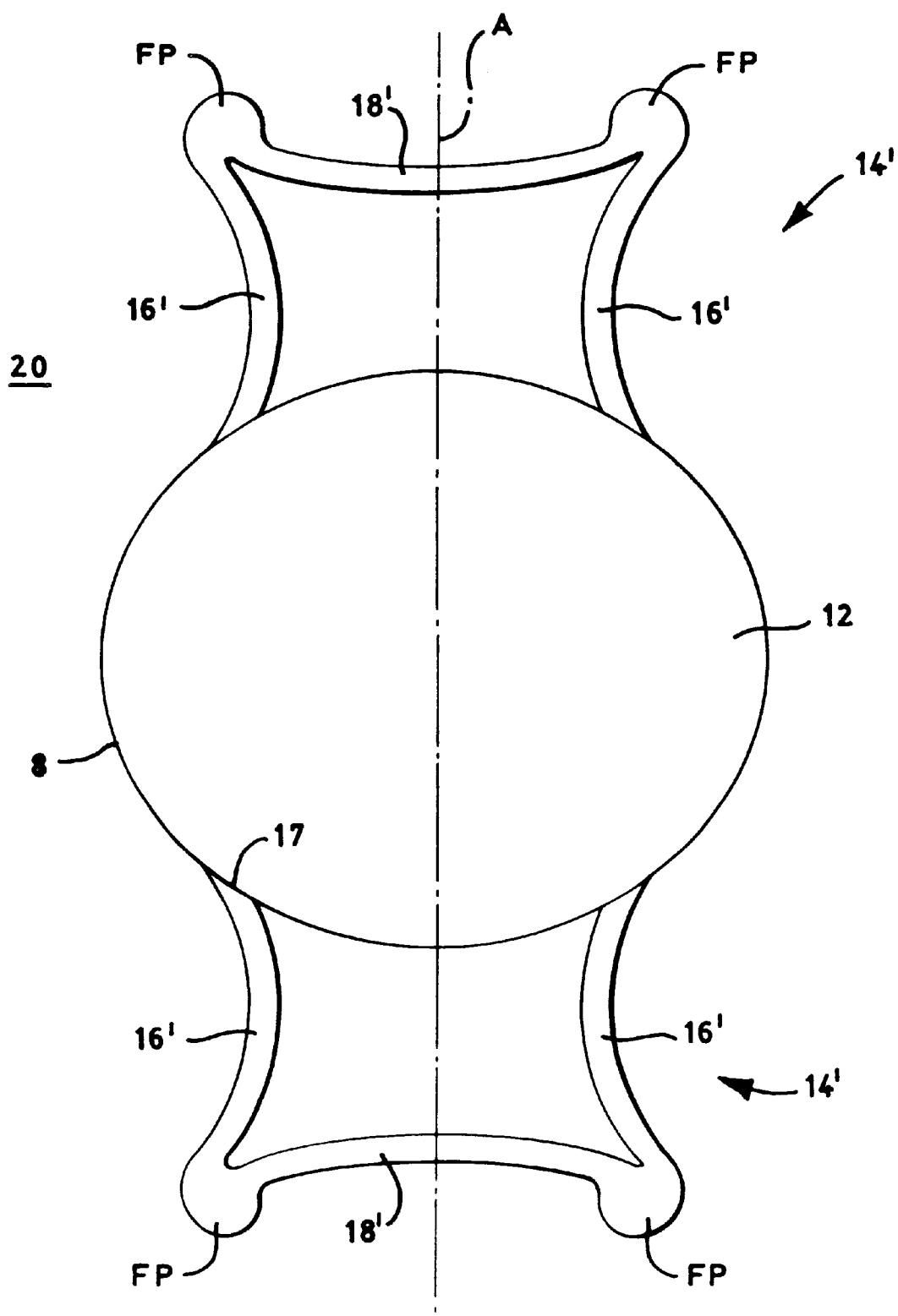
FIG. 4 shows a top view of alternative lens assembly of the invention.
Figure 5A:
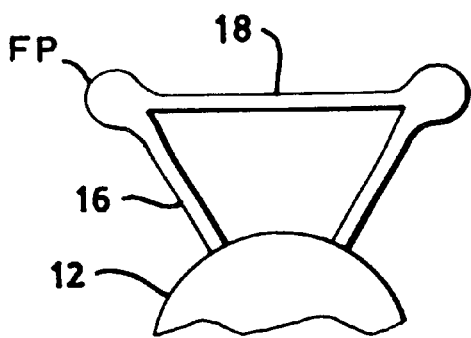
FIG. 5 shows alternate embodiments of the lens assembly.
Figure 5D:
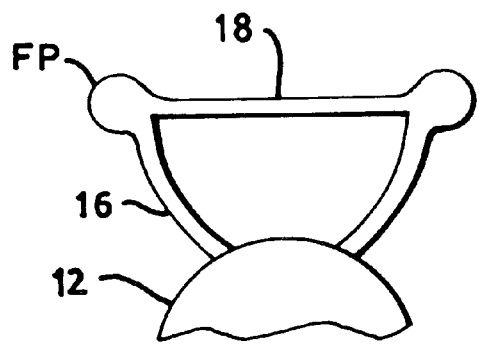
Figure 5B:
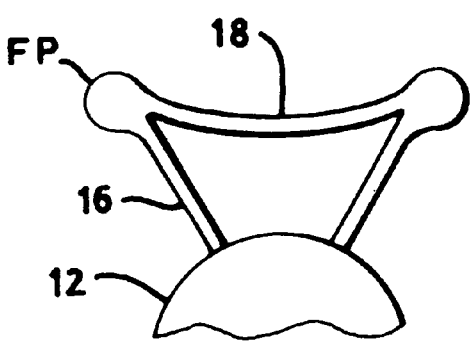
Figure 5E:
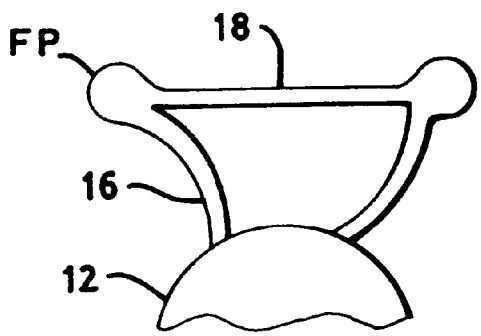
Figure 5C:
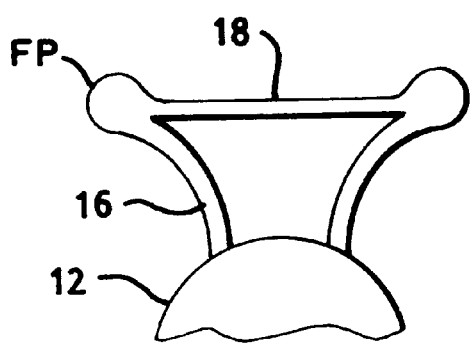
Figure 5F:
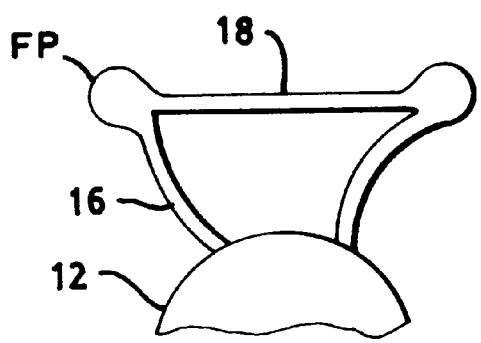
Figure 5G:
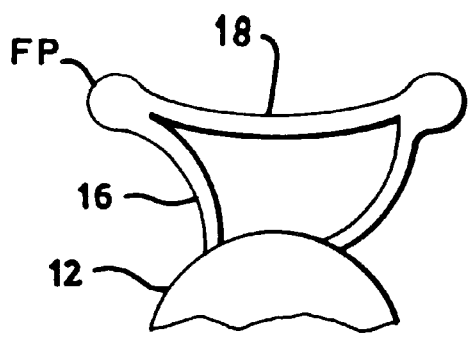
Figure 5H:
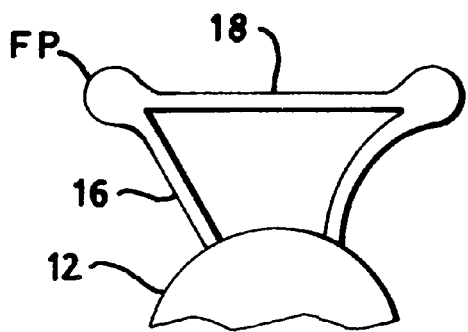
Figure 5I:
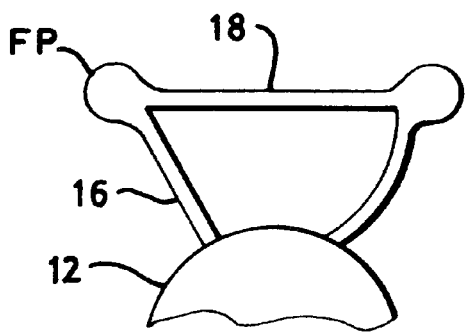
Figure 5J:
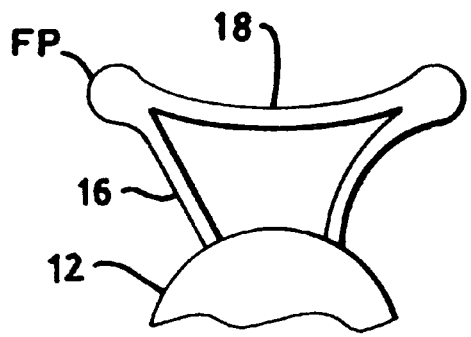
Figure 5K:
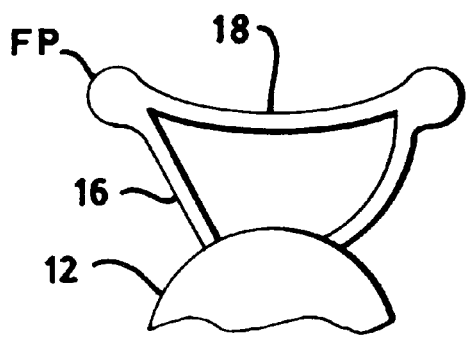
Figure 6:
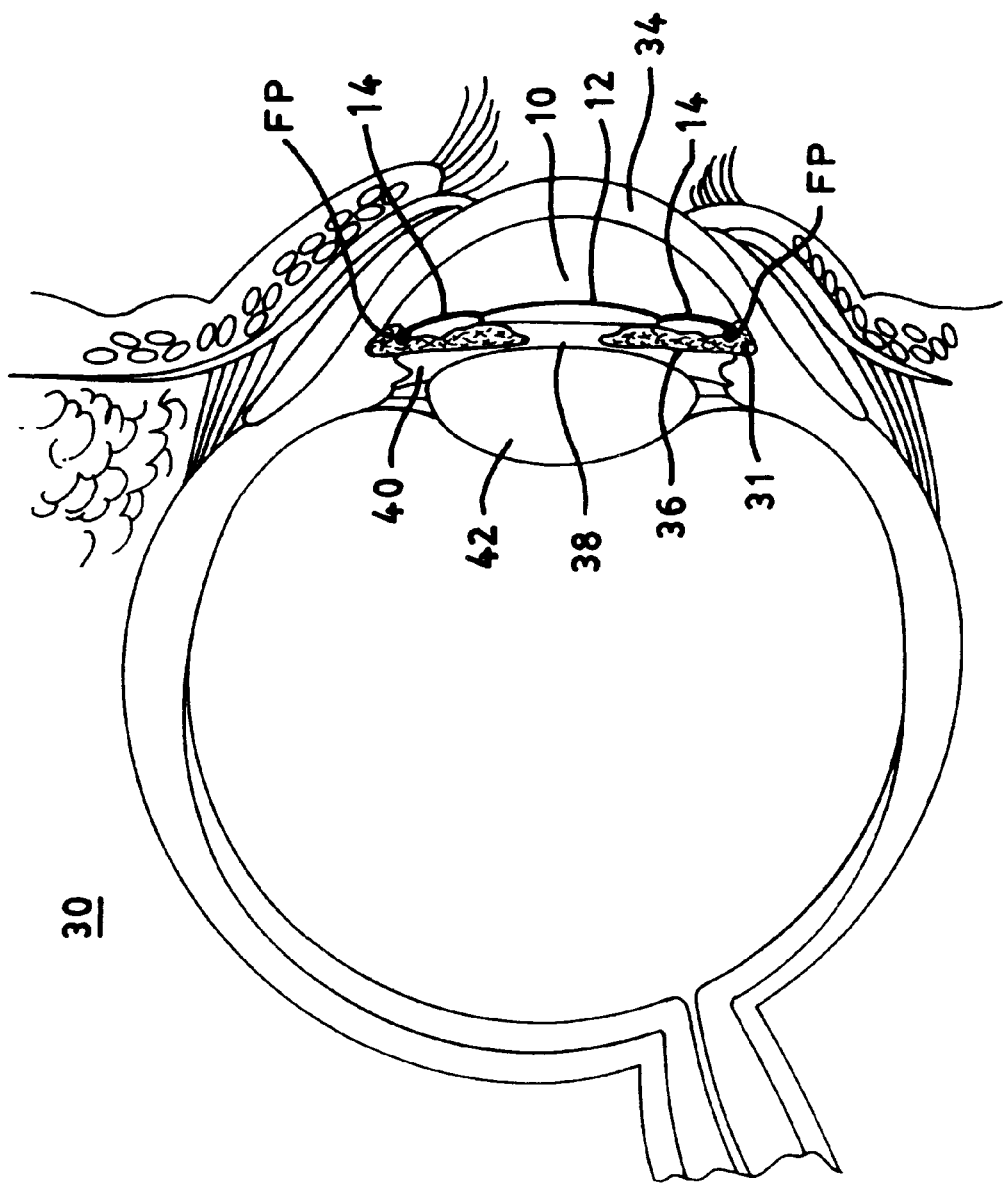
FIG. 6 shows a sectional view of an eye with the lens assembly of the invention deployed.

An alternate embodiment of the invention is shown in FIG. 4. In that figure, lens assembly 20 includes an optic 12 and haptics 14'. Lens assembly 20 is generally similar to the assembly 10 of FIG. 1 and 2, but has haptics 14' with inwardly bowing legs 16' in contrast to the assembly 10 that has haptics 14 with outwardly bowing legs 16. As with lens assembly 10, the lens assembly 20 is an anterior chamber angle supported intraocular lens preferably constructed of a biocompatible, foldable material such as hydrogel to allow for insertion through a clear corneal incision.

Other non-limiting configurations of haptics are shown in FIGS. 5A–K. In these embodiments, one or both of legs 16 of each haptic can be straight, inwardly bowing, outwardly bowing, or combinations thereof. Each haptic may have the same or different leg configurations as the other haptic.

In all embodiments, the transverse member 18 may be substantially straight or inwardly bowing. 'Substantially straight' includes either straight or slight, outward-bowing deviations from straight, provided that the outward bow of the transverse member 18 does not extend beyond the footplates FP in the direction of axis A in a manner that interferes with the footplates resting in the angle of the eye (see FIG. 1).

The preferred embodiment intraocular lens assembly of the invention is designed to be foldable to facilitate insertion through small incisions, generally 3 mm in length or less. The device can be folded along axis A (shown in FIG. 1), transverse to axis A, at an angle offset from axis A, or in multiple directions. The device can be folded in the optic body, at any point in the haptics, at the junction points between the optic body and the haptics, or all of the above. The device can be folded with single or multiple folds along each direction.

Suitable materials for the lens assembly of the invention are solid, flexible, foldable optical, non-biodegradable materials such as hydrogel, collamer, collagel (hydrogel-collagen blends) acrylic polymers, polymethylmethacrylage (PMMA) and silicone polymers. The lens assembly may also be made of a composite of materials, i.e. where the haptics are fabricated from one material and the optics from another material, for example, acrylic optics and hydrogel haptics. Where the lens assembly is used in the aphakic eye, flexible, but less foldable, materials may be preferred. For example, for the aphakic eye, the lens assembly may be made of all PMMA or a composite of PMMA optics and prolene haptics.

By way of example, the lens assembly may be made as a sterile UV-absorbing acrylic foldable form, for example using the same material as the AcrySof™ IOL manufactured by Alcon Laboratories, Inc. Moreover, in various forms the lens may be used in the anterior chamber, the posterior chamber sulcus and the posterior chamber bag.

FIG. 5 shows the intraocular lens device 10 of the invention implanted in the anterior chamber 32 of the eye 30 and fixated in the angle 31. Lens assembly 10 is positioned in anterior chamber 32, between cornea 34 and iris 36, with optic body 12 positioned over pupil 38 and haptics 14, with footplates FP extending into angle 31. Movement of natural crystalline lens 42 is unobstructed in the posterior chamber 40 by device 10. The low vault height insures that device 10 does not contact cornea 34.

With this configuration, the footplates of intraocular lens rests in angle 31, which steadies the intraocular lens in the proper position. No sutures or other securing mechanisms are needed. Furthermore, there is minimal contact or interference with the eye structures.

It will be apparent to those skilled in the art that other changes and modifications can be made in the above-described invention and methods for making and using the same, without departing from the scope of the invention herein, and it is intended that all matter contained in the above description shall be interpreted in an illustrative and not in a limiting sense.

What is claimed is:

1. An intraocular lens assembly comprising:
   a lens having a circumferential edge, and a first haptic and a second haptic, said first and second haptics extending from said lens, wherein each of said haptics include:
   i) a first leg extending from said edge to a distal end thereof;
   ii) a second leg extending from said edge to a distal end thereof; and
   iii) a transverse member extending between said distal ends of said first and second legs, said transverse member being substantially straight or bowed inward toward said lens, and
   including a footplate at each of said distal ends.

2. The lens assembly according to claim 1 wherein said first leg is selected from the shapes consisting of inwardly bowing, straight, and outwardly bowing.

3. The lens assembly according claim 1 wherein said second leg is selected from the shapes consisting of inwardly bowing, straight, and outwardly bowing.

4. The lens assembly according to claim 1 wherein said first and said second legs of said first and second haptic are the same shape.

5. The lens assembly according to claim 1 wherein said first and second legs of said first and second haptics are differently shaped.

6. The lens assembly according to claim 1 wherein each of said first and second legs of each of said first and second haptics is outwardly bowing.

7. The lens assembly according to claim 1 wherein each of said first and second legs of each of said first and second haptics is inwardly bowing.

8. The lens assembly according to claim 1 wherein the lens assembly is made from a flexible material.

9. The lens assembly according to claim 8 made of a material selected from the group consisting of hydrogel, collagen, collamar, collagel, acrylate polymers, methacrylate polmers, silicone polymers, and composites thereof.

10. A lens assembly according claim 9 wherein said lens assembly is foldable.

11. A lens assembly according to claim 9 wherein said lens assembly is firm.

12. A method of correcting hyperopia, myopia or astigmatism in the eye a patient in need of such correction comprising:
    implanting into the eye an intraocular lens assembly,
    said lens assembly having a lens and a first haptic and a second haptic,
    said lens having a circumferential edge, said first and second haptics extending from said edge, wherein each of said haptics includes:
    i) a first leg extending from said edge to a distal end thereof;
    ii) a second leg extending from said edge to a distal end thereof; and
    iii) a transverse member extending between said distal ends of said first and second legs, said transverse member being substantially straight or bowed inward toward said lens, and
    including a footplate at each of said distal ends.

13. The method according to claim 12 wherein said first leg is selected from the shapes consisting of inwardly bowing, straight, and outwardly bowing.

14. The method according to claim 12 wherein said second leg is selected from the shapes consisting of inwardly bowing, straight, and outwardly bowing.

15. The method according to claim 12 wherein said first and said second legs of said first and second haptic are the same shape.

16. The method according to claim 12 wherein said first and second legs of said first and second haptics are differently shaped.

17. The method according to claim 12 wherein each of said first and second legs of each of said first and second haptics is outwardly bowing.

18. The method according to claim 12 wherein each of said first and second legs of each of said first and second haptics is inwardly bowing.

19. The method according to claim 12 wherein the lens assembly is made from a flexible material.

20. The method according to claim 19 made of a material selected from the group consisting of hydrogel, collagen, collamar, collagel, acrylate polymers, methacrylate polmers, silicone polymers, and composites thereof.

21. The method according to claim 20 wherein said lens assembly is foldable.

22. The method according to claim 20 wherein said lens assembly is firm.

\* \* \* \* \*